United States Patent [19]

Merry et al.

[11] 4,301,813
[45] Nov. 24, 1981

[54] URINE METER

[75] Inventors: Jack D. Merry, Summerville, S.C.; William J. Dunn, Libertyville, Ill.

[73] Assignee: The Kendall Company, Boston, Mass.

[21] Appl. No.: 139,303

[22] Filed: Apr. 11, 1980

[51] Int. Cl.³ .......................... A61B 5/00; A61B 19/00
[52] U.S. Cl. ...................................... 128/762; 73/219; 128/767; 128/768; 128/771
[58] Field of Search ............... 128/762, 767, 768, 771, 128/295; 73/219, 426, 429

[56] References Cited

U.S. PATENT DOCUMENTS

| Re. 26,964 | 10/1970 | Coanda | 128/771 X |
|---|---|---|---|
| 3,001,397 | 9/1961 | Leonard | 73/219 X |
| 3,374,939 | 3/1968 | McMenimen | 128/295 |
| 3,661,143 | 5/1972 | Henkin | 128/767 X |
| 3,683,894 | 8/1972 | Villari | 128/771 X |
| 4,000,649 | 1/1977 | Hanifl | 128/767 X |
| 4,095,589 | 6/1978 | Manschot et al. | 128/771 X |

FOREIGN PATENT DOCUMENTS

| 1007533 | 3/1977 | Canada | 128/771 |
|---|---|---|---|
| 2308511 | 8/1973 | Fed. Rep. of Germany | 128/771 |
| 2289165 | 5/1976 | France | 128/771 |

Primary Examiner—Kyle L. Howell
Attorney, Agent, or Firm—Powell L. Sprunger

[57] ABSTRACT

A urine meter comprising, a container having a cavity for collection of urine, and a receptacle having a chamber to receive urine and being closed to the atmosphere in the receptacle. The meter communicates between an upper portion of the receptacle and an upper portion of the container, with a first channel for the passage of urine from the receptacle to the container and a second channel for the passage of air from the container to the receptacle.

9 Claims, 4 Drawing Figures

URINE METER

BACKGROUND OF THE INVENTION

The present invention relates to urine receptacles, and more particularly to urine meters.

Before the present invention, urine meters have been proposed of the type having a container, a receptacle, and a drainage tube communicating with an upper portion of the receptacle. The receptacle may be used to determine incoming urine volumes with relative accuracy, and the receptacle may be periodically emptied into the container where the urine is stored. However, in the past it has been necessary to provide the receptacle with a vent to alleviate a vacuum in the receptacle when the urine is emptied into the container. Such vents have frequently become blocked causing a vacuum condition in the receptacle when the urine is emptied into the container. Also, the vents have been an unduly costly item for the urine meters.

SUMMARY OF THE INVENTION

A principal feature of the present invention is the provision of an improved urine meter for receiving urine from a patient.

The urine meter comprises, a container having a cavity for collecting urine, and a receptacle having a chamber to receive urine. The urine meter has means communicating between an upper portion of the receptacle and an upper portion of the container including first and second channel means.

A feature of the present invention is that the first channel means permits the passage of urine from the receptacle to the container when the receptacle is placed in a tilted configuration.

Another feature is that the second channel means permits the passage of air from the container to the receptacle when the urine is emptied from the receptacle into the container.

Yet another feature of the invention is that the urine meter permits exchange of air between the container and receptacle, thus eliminating the need for a vent on the receptacle.

Still another feature of the invention is that the urine meter may be made at a reduced cost due to elimination of the vent on the receptacle.

Further features will become more fully apparent in the following description of the embodiments of this invention and from the appended claims.

DESCRIPTION OF THE PREFERRED EMBODIMENTS

Figure 1:
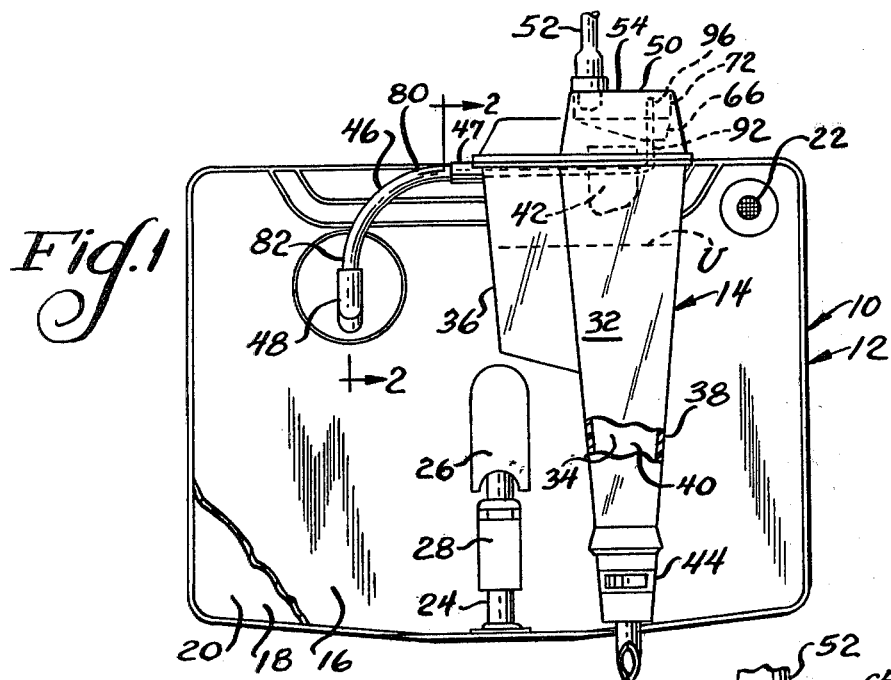
FIG. 1 is a fragmentary front plan view of a urine meter of the present invention.

Referring now to FIG. 1, there is shown a urine meter generally designated 10 having a container 12 and a receptacle 14. The container 12 has a front wall 16 and a rear wall 18 of flexible material, such as a suitable plastic, being joined together around the periphery thereof and defining a cavity 20 between the front and rear walls 16 and 18. The front wall 16 of the container 12 has a vent 22 with a bacteria filter of known type communicating with the container cavity 20. The container 12 has a tubular section 24 communicating with a lower portion of the cavity 20, and having an outer end removably received in a pocket 26, with the tubular section 24 having a releasable clamp 28 on the tubular section. Thus, when it is desirable to drain urine from the container 12, the tubular section 24 is removed from the pocket 26, and the clamp 28 is released to permit passage of urine through the tubular section 24. The container 12 may also have a string (not shown) attached to an upper portion of the container 12 to permit hanging of the urine meter 10 from a suitable object during use.

Figures 2, 3:
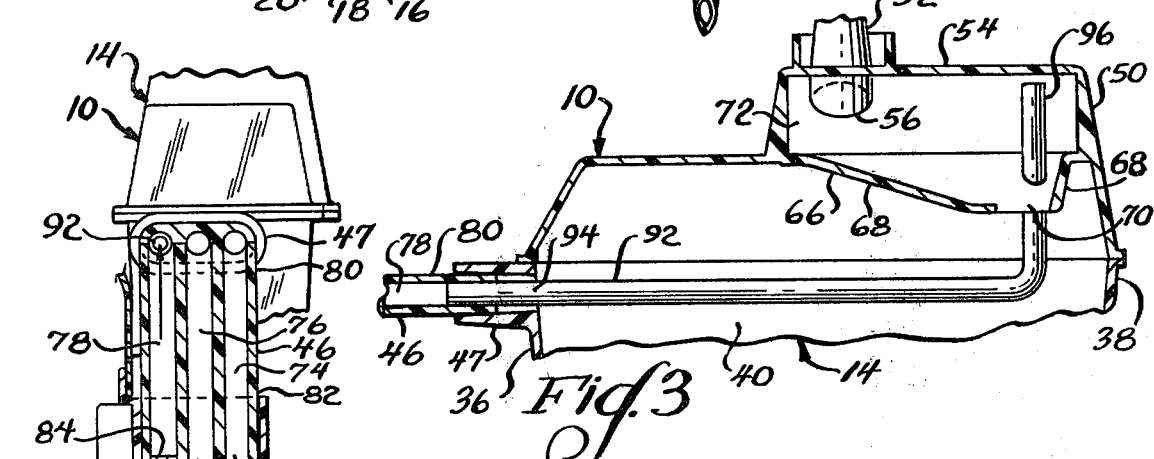
FIG. 2 is a fragmentary sectional view taken substantially as indicated along the line 2—2 of FIG. 1.
FIG. 3 is a fragmentary sectional view of an upper portion of a receptacle on the urine meter of FIG. 1.

With reference to FIGS. 1-3, the receptacle 14 has a front wall 32, a rear wall 34, and a pair of side walls 36 and 38 defining a chamber 40 in the receptacle 14. The receptacle 14 has a hook 42 extending from the rear wall 34 and spaced from the rear wall 34 to receive an upper portion of the container 12 in order to support the receptacle 14 on the upper portion of the container 12. The receptacle 14 has a lower valve 44 to permit draining of urine when desired from the receptacle chamber 40 to obtain a specimen of urine. The urine meter 10 has a flexible tubular section 46 having one end connected to the receptacle 14 by a connector 47 adjacent the side wall 36 such that it communicates with an upper portion of the chamber 40, and the other end of the tubular section 46 is attached by a connector 48 to an upper portion of the container 12 on the front wall 16, such that the tubular section 46 communicates with an upper portion of the cavity 20. Thus, the tubular section 46 communicates between an upper portion of the chamber 40 and an upper portion of the cavity 20 as will be further described below.

As shown, the receptacle 14 has a raised portion 50 adjacent an upper end of the receptacle 14. The urine meter 10 has a drainage tube 52 for draining urine from the patient, with a downstream end of the drainage tube 52 extending through an upper wall 54 of the raised portion 50 into the receptacle 14 to define a drip tube 56 inside the receptacle 14. As shown, the receptacle 14 has a baffle 66 extending across the lower part of the raised portion 50, with the baffle 66 having downwardly sloping walls 68 defining a lower opening 70 adjacent the side wall 38. The baffle 66 defines a compartment 72 in the raised portion 50, with the drip tube 56 being located in the compartment 72 above the walls 68 of the baffle 66.

As shown, the tubular section 46 has first, second, and third lumens or channels 74, 76, and 78, respectively. One end 80 of the tubular section 46 is received in the connector 47, and the other end 82 of the tubular section 46 is received in the connector 48 in order to attach the tubular section 46 between the receptacle 14 and the container 12. With reference to FIG. 2, the connector 48 may have a tubular section 84 received in the third lumen 78. Also, the connector 48 has a flange 86 defining a first lower port 88, and a second upper port 90, with the first and second channels 74 and 76 communicating with the first port 88, and with the third channel 78 communicating with the second port 90. Thus, the first and second channels 74 and 76 communicate with the container at a location below the position where the third lumen 78 communicates with the container 12. As shown in FIG. 3, the urine meter 10 has a conduit 92 having one end 94 received in the one end 80 of the tubular section 46 such that the conduit 92 communicates with the third lumen 78. The conduit 92 extends across the receptacle 14, and passes through the baffle 66 with the conduit having an open end 96 located in the compartment 72 above the baffle 66. In this manner, the third channel 78 and conduit 92 communicate between the upper second port 90 of the container 12 and the compartment 72 of the receptacle 14.

In use, urine drains from a catheter (not shown) in the patient through the drainage tube 52 and drip tube 56 into the compartment 72, where it drains along the wall 68 of the baffle 66 through the opening 70 into the receptacle chamber 40. As the urine collects in the chamber 40 of the receptacle 14, the volume of urine may be determined by suitable indicia (not shown) on the front wall 32 of the receptacle 14. When a suitable volume of urine U has been collected in the receptacle chamber 40, as shown in FIG. 1, the urine may be emptied into the container 12 for retention therein.

Figure 4:
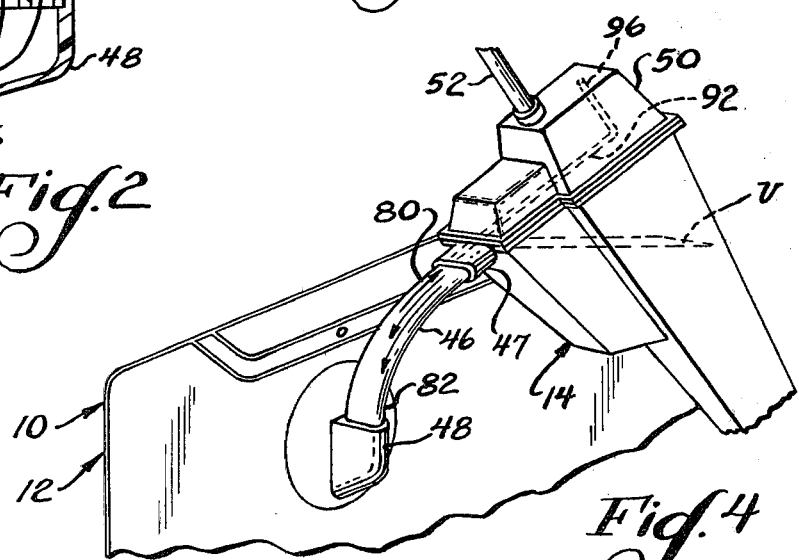
FIG. 4 is a fragmentary front plan view of the urine meter showing the receptacle being tilted to pass urine into a container of the urine meter.

In order to accomplish this result, the receptacle 14 is lifted from the container 12 to remove the hook 42 from the upper portion of the container 12, and the receptacle 14 is then tilted, as shown in FIG. 4, such that urine U passes through the first and second channels 74 and 76 and the lower port 88 in the connector 48 to the cavity 20 of the container 12. As urine passes from the receptacle 14 to the container 12, a vacuum is created in the receptacle chamber 40 causing air to pass from the upper port 90 through the third channel 78 and conduit 92 into the compartment 72 and chamber 40 of the receptacle 14. In this manner, air is displaced from the container cavity 20 to the receptacle chamber 40 as the urine is emptied into the container 12 from the receptacle 14. Thus, the urine meter of the present invention provides a receptacle 14 which is closed to the atmosphere, and eliminates the need for a vent on the receptacle 14. In this manner, the urine meter 10 of the invention reduces the cost of the urine meter to the patient, and eliminates possible vacuum conditions in the receptacle which otherwise might be caused by vent blockage on the receptacle.

In the described manner, the urine U is transferred from the receptacle 14 to the container 12 in order to initiate collection of a new volume of urine in the receptacle 14. When the receptacle 14 is tilted to pass urine into the container 12, the baffle 66 prevents passage of urine into the drip tube 56 and into the open end 96 of the conduit 92 in the event that the receptacle is tilted too far during the emptying procedure. Thus, the baffle 66 eliminates the possibility that urine may reflux into the drip tube 56 and drainage tube 52 in order to minimize the possibility of retrograde bacteria movement into the drainage tube 52 and possibly the patient. Also, the baffle 66 prevents passage of urine into the conduit 92, while the conduit 92 prevents passage of urine into the third lume 78, in order to assure that air is permitted to pass from the container 12 to the receptacle 14 during the emptying procedure.

The foregoing detailed description is given for clearness of understanding only, and no unnecessary limitations should be understood therefrom, as modifications will be obvious to those skilled in the art.

We claim:

1. A urine meter, comprising:
   a container having a cavity for collection of urine;
   a receptacle having a chamber to receive urine and being closed to the atmosphere in the receptacle;
   a drainage tube having a downstream and communicating with an upper portion of the receptacle; and
   means communicating between an upper portion of the receptacle and an upper portion of the container, including first channel means for the passage of urine from the receptacle to the container and second channel means for the passage of air from the container to the receptacle.

2. The meter of claim 1 wherein the communicating means comprises a tubular section connected between an upper portion of the receptacle and an upper portion of the container, said tubular section having a first channel communicating between the chamber and cavity for passage of urine from the chamber to the cavity, and a second channel communicating between the chamber and cavity for passage of air from the cavity to the chamber.

3. The meter of claim 2 wherein the tubular section has a pair of channels communicating between the chamber and cavity for passage of urine from the chamber to the cavity.

4. The meter of claim 2 wherein the tubular section includes a conduit in the receptacle chamber communicating with said second channel, said conduit having an open end located adjacent an upper end of the receptacle.

5. The meter of claim 4 wherein said receptacle includes a baffle extending across an upper portion of the receptacle, and in which said conduit extends through the baffle with said open end being located above said baffle.

6. The meter of claim 2 in which the first channel communicates with the container at a location below the position where the second channel communicates with the container.

7. The meter of claim 1 wherein said container has a vent.

8. The meter of claim 1 wherein said receptacle is relatively rigid and in which said container has a pair of opposed flexible walls defining the cavity.

9. The meter of claim 1 including means for releasably supporting the receptacle over a front wall of the container.

* * * * *